United States Patent
Johnston et al.

(10) Patent No.: US 11,738,170 B2
(45) Date of Patent: Aug. 29, 2023

(54) FLUSHING STYLET

(71) Applicant: MOZARC MEDICAL US LLC, Minneapolis, MN (US)

(72) Inventors: Thomas M. Johnston, Westborough, MA (US); Ty Fairneny, Hopkinton, MA (US)

(73) Assignee: Mozarc Medical US LLC, Minneapolis, MN (US)

( * ) Notice: Subject to any disclaimer, the term of this patent is extended or adjusted under 35 U.S.C. 154(b) by 356 days.

(21) Appl. No.: 17/127,011

(22) Filed: Dec. 18, 2020

(65) Prior Publication Data

US 2021/0100975 A1 Apr. 8, 2021

Related U.S. Application Data

(60) Division of application No. 16/361,638, filed on Mar. 22, 2019, now abandoned, which is a continuation of application No. 13/792,411, filed on Mar. 11, 2013, now Pat. No. 10,279,143.

(51) Int. Cl.
*A61M 25/00* (2006.01)
*A61M 1/36* (2006.01)
*A61M 25/01* (2006.01)

(52) U.S. Cl.
CPC ...... *A61M 25/0017* (2013.01); *A61M 1/3661* (2014.02); *A61M 25/0108* (2013.01); *A61M 2025/0019* (2013.01)

(58) Field of Classification Search
CPC ...... A61M 2025/0019; A61M 25/0017; A61M 25/1011
See application file for complete search history.

(56) References Cited

U.S. PATENT DOCUMENTS

| | | |
|---|---|---|
| 4,968,306 A | 11/1990 | Huss et al. |
| 5,059,176 A | 10/1991 | Winters |
| 5,380,307 A | 1/1995 | Chee et al. |
| 5,425,723 A | 6/1995 | Wang |
| 5,533,516 A | 7/1996 | Sahatjian |
| 5,669,879 A | 9/1997 | Duer |
| 5,876,376 A | 3/1999 | Schwab et al. |

(Continued)

OTHER PUBLICATIONS

Prosecution History from U.S. Appl. No. 13/792,411, dated Aug. 12, 2014 through Feb. 8, 2019, 242 pp.

(Continued)

*Primary Examiner* — William R Carpenter
(74) *Attorney, Agent, or Firm* — Shumaker & Sieffert, P.A.

(57) ABSTRACT

A stylet includes an elongate body defining a passage and at least one aperture in fluid communication with the passage. The stylet also includes a first blocking dam secured to the elongate body proximal to the at least one aperture and a second blocking dam secured to the elongate body distal to the at least one aperture. The stylet is movable within a lumen of a catheter to a position in which the first and second blocking dams are, respectively, proximal and distal to at least one side opening of the catheter and each of the first and second blocking dams is sealingly engaged with an inner surface of the catheter such that fluid introduced into the lumen, from the passage and through the at least one aperture of the stylet, is directed through the at least one side opening of the catheter.

20 Claims, 9 Drawing Sheets

(56) References Cited

U.S. PATENT DOCUMENTS

| | | |
|---|---|---|
| 5,941,871 A | 8/1999 | Adams et al. |
| 5,964,004 A * | 10/1999 | Bean .................... B08B 9/0436 15/104.16 |
| 6,044,845 A | 4/2000 | Lewis |
| 6,190,353 B1 | 2/2001 | Makower et al. |
| 6,602,241 B2 | 8/2003 | Makower et al. |
| 6,623,452 B2 | 9/2003 | Chien et al. |
| 7,452,353 B2 | 11/2008 | Dal Porto et al. |
| 8,490,235 B2 * | 7/2013 | Soetermans .......... B08B 9/0436 15/104.16 |
| 8,702,678 B2 | 4/2014 | Comerota et al. |
| 8,814,847 B2 | 8/2014 | Hoffman et al. |
| 10,279,143 B2 | 5/2019 | Johnston et al. |
| 2001/0041862 A1 | 11/2001 | Glickman |
| 2002/0052576 A1 | 5/2002 | Massengale |
| 2002/0077594 A1 | 6/2002 | Chien et al. |
| 2002/0091352 A1 | 7/2002 | McGuckin, Jr. et al. |
| 2003/0176830 A1 | 9/2003 | Scheule |
| 2004/0199155 A1 | 10/2004 | Mollenauer |
| 2005/0020976 A1 | 1/2005 | Maki et al. |
| 2005/0107738 A1 | 5/2005 | Slater et al. |
| 2007/0213671 A1 | 9/2007 | Hiatt |
| 2009/0264860 A1 | 10/2009 | Hiatt |
| 2009/0270838 A1 | 10/2009 | Berthiaume et al. |
| 2009/0292241 A1 * | 11/2009 | Von Oepen ....... A61M 25/1029 264/299 |
| 2010/0057001 A1 | 3/2010 | Chen et al. |
| 2010/0063534 A1 | 3/2010 | Kugler et al. |
| 2010/0222811 A1 | 9/2010 | Gellman et al. |
| 2019/0217055 A1 | 7/2019 | Johnston et al. |

OTHER PUBLICATIONS

Prosecution History from U.S. Appl. No. 16/361,638, dated Mar. 25, 2019, through Dec. 18, 2020, 31 pp.

* cited by examiner

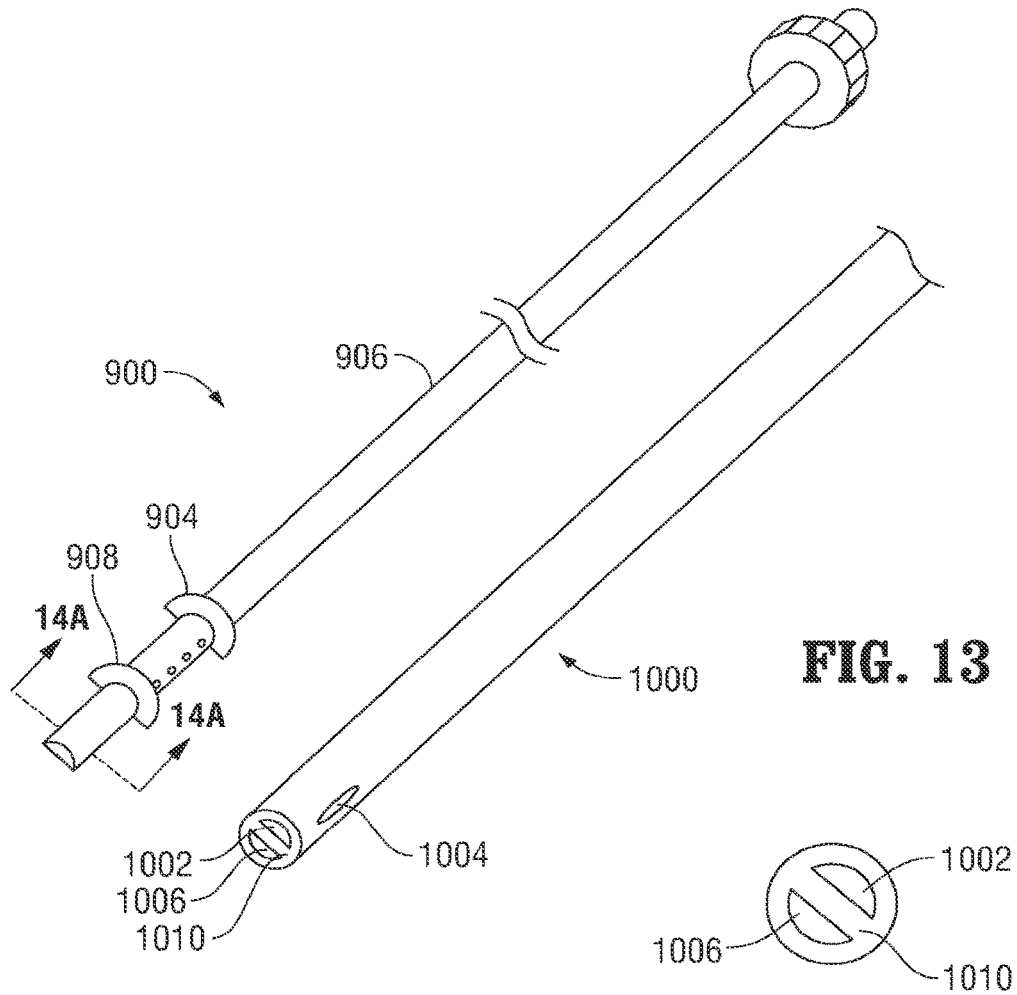
FIG. 13
FIG. 13A
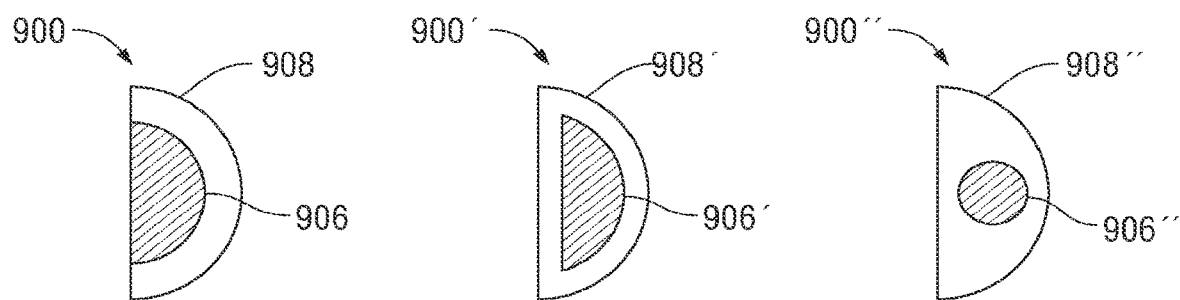
FIG. 14A  FIG. 14B  FIG. 14C

FLUSHING STYLET

This application is a divisional of U.S. patent application Ser. No. 16/361,638, filed Mar. 22, 2019, and entitled, "Flushing Stylet," which is a continuation of U.S. patent application Ser. No. 13/792,411, filed Mar. 11, 2013, and entitled, "Flushing Stylet"; the disclosure of each of the above-identified applications is hereby incorporated by reference in its entirety.

TECHNICAL FIELD

The present disclosure relates to catheters and catheter accessories, and more specifically, to a flushing stylet.

BACKGROUND

Catheters are flexible medical instruments used for withdrawal and/or introduction of fluids to and from body cavities, ducts, and vessels. Catheters have particular application in hemodialysis procedures, in which blood is withdrawn from a blood vessel for treatment and subsequently returned to the blood vessel for circulation through a patient's body.

Many hemodialysis catheters include multiple lumens, such as dual or triple-lumen catheters. One lumen is dedicated to withdrawal of fluid from a vessel, and at least one other lumen is dedicated to return of fluid to the vessel. Generally, the lumen through which fluid is withdrawn is referred to as the "arterial" lumen, and the lumen through which fluid is returned is referred to as the "venous" lumen. During a hemodialysis procedure, after placement of a multiple lumen catheter in a patient, blood is typically withdrawn from the patient through the arterial lumen of the catheter, and is directed to a hemodialysis unit for dialysis to remove waste and toxins from the blood. The dialyzed blood is then returned to the patient through the venous lumen of the catheter.

Generally, hemodialysis catheters are categorized as either acute or chronic. Acute catheters are designed to be placed in a patient under emergent circumstances, under which delays in placement are unacceptable. Acute catheters typically remain in place for only a few days. Chronic catheters, by comparison, typically remain in place for extended periods of time, and may be implanted via surgical dissection, which can be performed at the patient's bedside or in an ambulatory surgical setting.

Catheters, particularly chronic dialysis catheters, may be subject to thrombus formations following placement. These thrombus formations can restrict or block blood flow through the catheter, potentially lengthening the time required for treatment, compromising the efficacy of the treatment, and/or requiring more frequent replacement of the catheter. Methods of dislodging thrombus formations to restore proper fluid flow include forcing a solution through the catheter and/or, in the case of dialysis catheters, reversing the lines of the dialysis machine. Such treatments can be limited by the amount of fluid pressure that can be built up in the catheter. Moreover, such treatments can have limited efficacy in catheters with multiple openings, such as catheters with distal and side openings, because fluids moving through the catheter tend to bypass those openings with more significant blockages and exit through those openings that offer less resistance to flow.

SUMMARY

Systems and methods for clearing blockages from catheters are disclosed. In one aspect, a system includes a catheter and a stylet. The catheter includes a wall having an inner surface and an outer surface, the inner surface defining a lumen, and the wall defining at least one side opening extending from the outer surface to the inner surface defining the lumen.

The stylet includes an elongate body and first and second blocking dams. The elongate body defines a passage and at least one aperture in fluid communication with the passage. The first blocking dam is secured to the elongate body proximal to the at least one aperture. The second blocking dam is secured to the elongate body distal to the at least one aperture. The stylet is movable within the lumen to a position in which the first and second blocking dams are, respectively, proximal and distal to the at least one side opening of the catheter and each of the first and second blocking dams is sealingly engaged with the inner surface of the catheter such that fluid introduced into the lumen, from the passage and through the at least one aperture of the stylet, is directed through the at least one side opening of the catheter.

In some embodiments, the catheter defines an end orifice distal to the at least one side opening. In certain embodiments, the at least one aperture of the stylet includes a plurality of apertures axially aligned with one another, between the first and second blocking dams. In certain embodiments, the at least one aperture includes a plurality of apertures disposed about a circumference of the elongate body of the stylet. In some embodiments, the at least one aperture includes a plurality of apertures circumferentially and axially offset from each other.

The stylet can include a closed, tapered distal end.

The first and second blocking dams can each include an arcuate outer wall engageable with the inner surface of the lumen. Additionally or alternatively, the first and second blocking dams may include a lubricous coating.

In certain embodiments, the stylet includes a marker band disposed between the first and second blocking dams and extending around at least a portion of a circumference of the elongate body. The marker band can be viewable using one or more imaging techniques including fluoroscopy, magnetic resonance imaging, and x-ray.

In some embodiments, the first and second blocking dams are formed from a material that is more radiopaque than material forming the remainder of the stylet.

In another aspect of the present disclosure, a stylet for use with a catheter includes an elongate body, a first blocking dam, and a second blocking dam. The elongate body defines a passage and at least one aperture in fluid communication with the passage. The first blocking dam is secured to the elongate body proximal to the at least one aperture. The second blocking dam is secured to the elongate body distal to the at least one aperture. The elongate body is movable within a lumen of the catheter to a position in which the first and second blocking dams are, respectively, proximal and distal to a side opening of the catheter and each of the first and second blocking dams is sealingly engageable with an inner surface of the catheter such that fluid introduced into the lumen of the catheter, from the passage and through the at least one aperture of the stylet, is directed through the side opening of the catheter.

The at least one aperture may include a plurality of apertures axially aligned with each other between the first and second blocking dams. Additionally or alternatively, the at least one aperture can include a plurality of apertures disposed about a circumference of the elongate body.

The stylet includes a closed distal end, which may be tapered to facilitate, for example, passage of the stylet through the lumen of the catheter.

In some embodiments, the stylet includes a marker band extending around at least a portion of a circumference of the elongate body. For example, the marker band can be viewable using one or more imaging techniques including fluoroscopy, magnetic resonance imaging, and x-ray.

In another aspect of the present disclosure, methods are disclosed for increasing fluid flow through a catheter. The method includes advancing a stylet through a lumen of the catheter, orienting the stylet, and moving fluid through the stylet. The stylet is oriented such that a first blocking dam secured to an elongate body of the stylet is distal to a side opening defined by the catheter and a second blocking dam secured to the elongate body of the stylet is positioned proximal to the side opening. The fluid is moved through the stylet and into a space defined between the first and second blocking dams to create a zone of pressure between the elongate body of the stylet and an inner surface of the catheter, in fluid communication with the side opening defined in the catheter to remove a blockage from the side opening.

Orienting the stylet may include forming a seal between an inner surface of the lumen of the catheter and each of the first and second blocking dams.

The subject matter of the present disclosure may include one or more of the following advantages.

By incorporating first and second blocking dams that form a seal with an inner surface of a lumen defined by a catheter, a zone of pressure can be created in the axial space between the first and second blocking dams subsequent to the communication of fluid into the stylet. Because the seal formed between the inner surface of the lumen and each of the first and second blocking dams closes off the remaining portions of the lumen, pressure can be applied to a blockage obstructing the side opening of the catheter, regardless of whether the distal opening of the catheter is blocked.

Additionally or alternatively, creating a zone of pressure can reduce the need to align the aperture in the stylet with the side opening in the catheter, as compared to stylets without first and second blocking dams that may be used to attempt to remove a blockage in a side opening of a catheter.

Moreover, by applying pressure to the blockage through the creation of a zone of pressure in the axial space between the first and second blocking dams, a single aperture may be used, as compared to other stylets which may generally require multiple apertures to apply fluid directly toward the blockage.

Further still, by creating a zone of pressure that is much smaller than the entire length of the catheter, less fluid will be needed to provide the pressure necessary to dislodge a blockage. This can, for example, reduce the time necessary to perform the procedure.

Other aspects, features, and advantages of the presently disclosed subject matter will be apparent from the description, the drawings, and the claims.

BRIEF DESCRIPTION OF THE DRAWINGS

FIG. 13 is a side, perspective view of a stylet and a catheter.

FIG. 13A is an end view of the catheter seen in FIG. 13.

FIG. 14A is a transverse, cross-sectional view taken through lines 14-14 in FIG. 13.

FIG. 14B is a transverse, cross-sectional view of a stylet.

FIG. 14C is a transverse, cross-sectional view of a stylet.

DETAILED DESCRIPTION OF EMBODIMENTS

Figure 1:
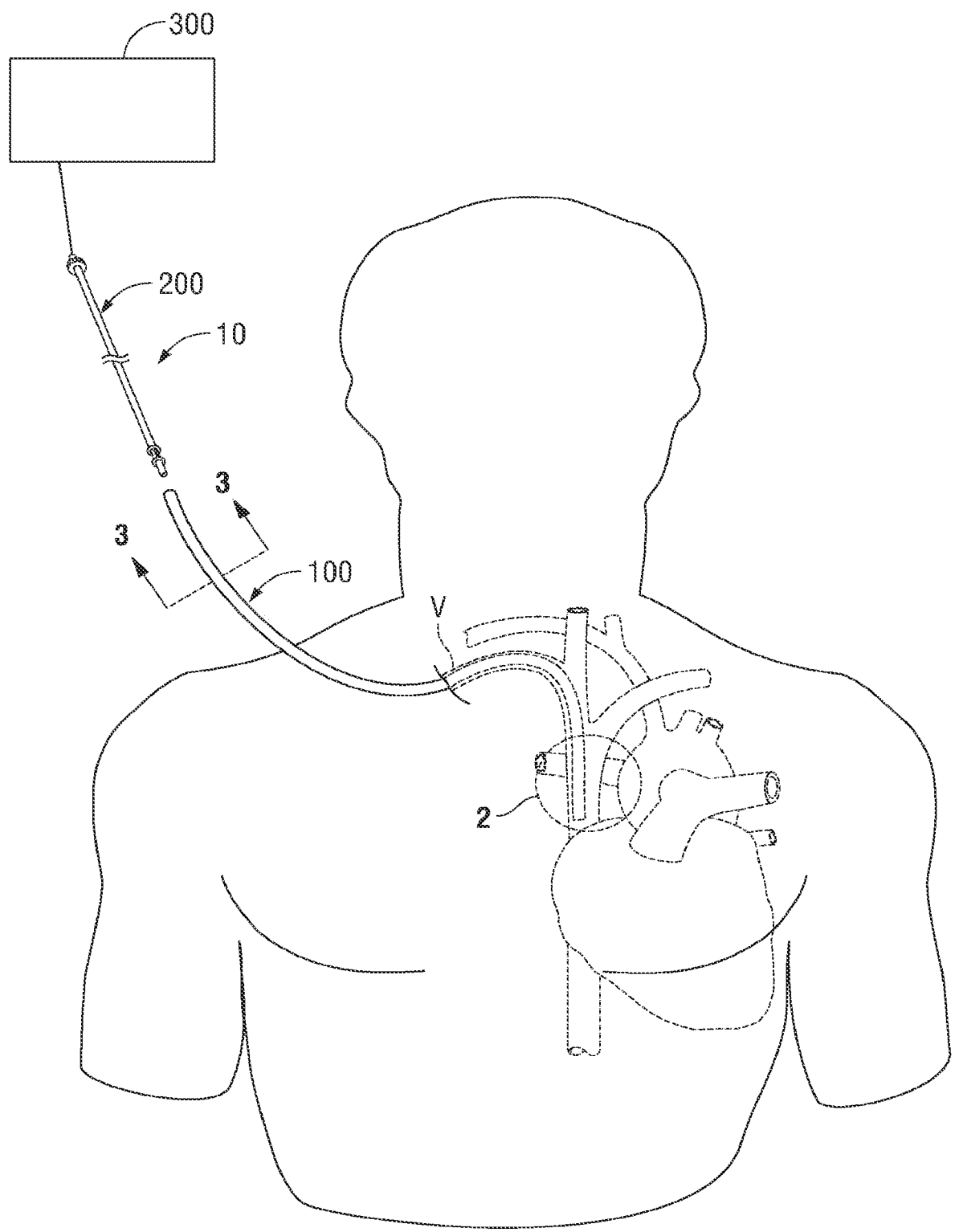
FIG. 1 is a schematic of a system for use in a medical procedure including a catheter and a stylet.

Embodiments of the present disclosure will now be described in detail with reference to the drawings, wherein like reference numerals identify similar or identical elements. As used herein, the term "patient" refers to a human patient or other animal, and the term "clinician" refers to a doctor, nurse, support personnel, or other care provider. Additionally, the term "distal" refers to that portion of a device, or a component thereof, furthest from the clinician during proper use, while the term "proximal" refers to that portion of a device, or a component thereof, closest to the clinician during proper use.

Embodiments of the present disclosure are discussed below in terms of hemodialysis catheters. However, the principles of the present disclosure are applicable to a range of catheter applications including peritoneal dialysis, surgical, diagnostic, and related treatments of diseases and body ailments, such as, for example, the administration and removal of medication, saline, bodily fluids, and urine. The principles of the present disclosure are applicable to a variety of catheter-related procedures, such as, for example, cardiac, abdominal, urinary, and intestinal procedures, in chronic and acute applications.

Figure 2:
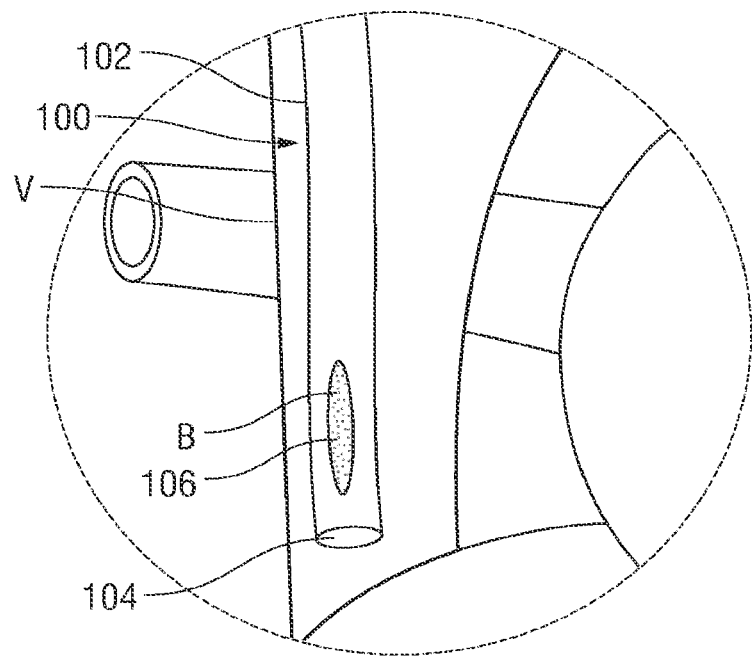
FIG. 2 is an enlargement of the area of detail indicated in FIG. 1.

Referring now to FIGS. 1 and 2, a system 10 for use in an exemplary medical procedure, such as a dialysis procedure, includes a catheter 100 and a stylet 200. The catheter 100 defines a side opening 106 and, in use, the catheter 100 is positioned within a blood vessel V such that blood can be withdrawn from the blood vessel V and into the catheter 100 through the side opening 106. Dialyzed blood can be subsequently returned to the blood vessel V through the side opening 106 or through another opening. Over time, particularly over periods associated with chronic catheters, thrombus formation may occur on the outer surface of the catheter 100 and/or in the side opening 106, resulting in a blockage B that restricts or occludes blood flow through the catheter 100. As described in further detail below, a clinician may remove the blockage B by advancing the stylet 200 through the catheter 100 to the vicinity of the side opening 106 and moving pressurized fluid from a fluid source 300, through the stylet 200, and toward and through the side opening 106. The mechanical force of the pressurized fluid moving through the side opening 106 can dislodge the blockage B from the side opening 106. Additionally or alternatively, chemical activity of the pressurized fluid (e.g., in the case of heparinized saline) can act to remove the blockage B from the side opening 106. As used herein, the term "blockage" includes any flow restriction inhibiting flow through the side opening 106, such as, for example, thrombus arid/or plaque. In addition, for clarity of explanation, a single side opening 106 is shown. However, it should be appreciated that the catheter 100 can define multiple side openings 106 without departing from the scope of the present disclosure. For example, the stylet 200 can be configured and used to remove blockages B from multiple side openings 106.

Figure 3:
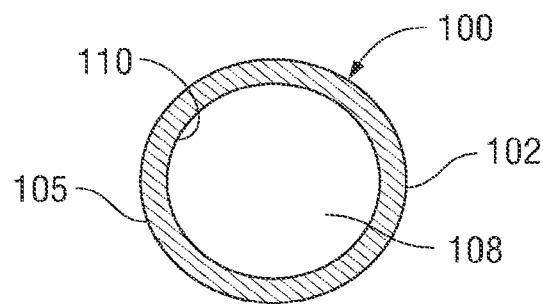
FIG. 3 is a transverse, cross-sectional view taken through lines 3-3 in FIG. 1.
Figure 4:
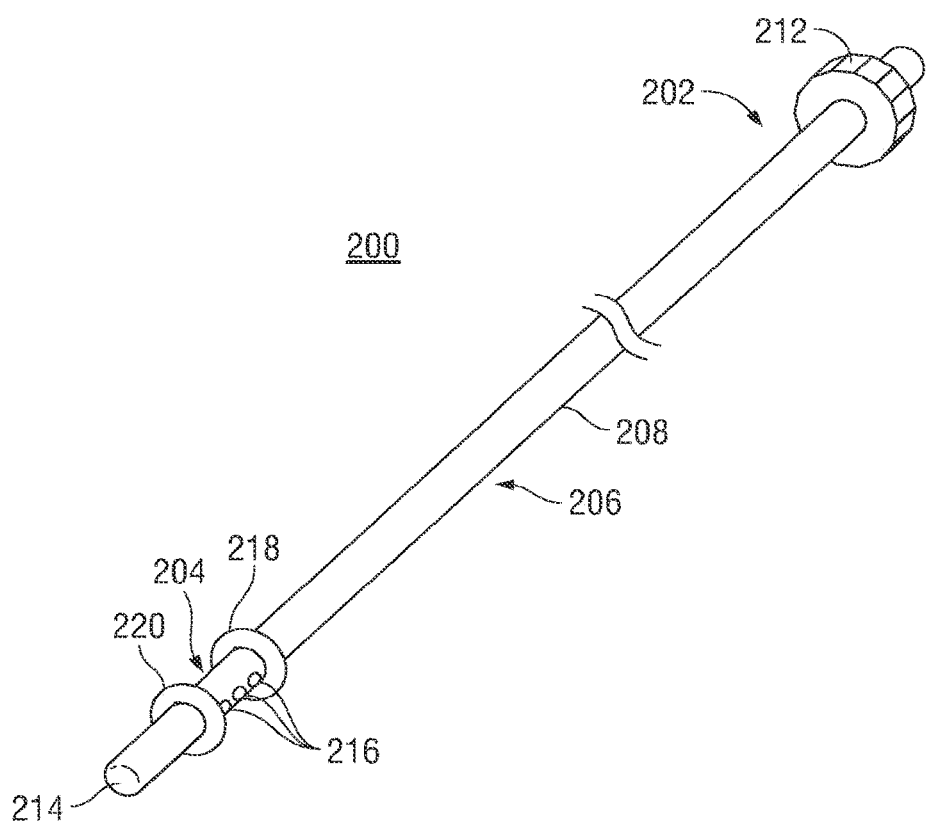
FIG. 4 is a side, perspective view of the stylet of FIG. 1.
Figure 5:
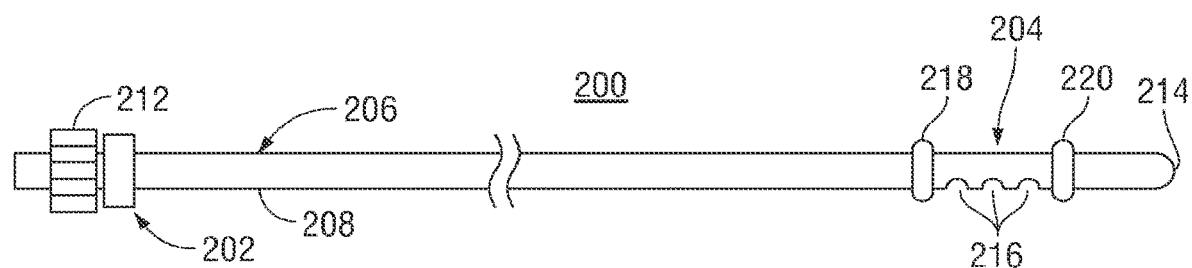
FIG. 5 is a side, plan view of the stylet of FIG. 1.

Referring now to FIGS. 1-3, the catheter 100 includes a wall 102 having an inner surface 110 and an outer surface 105. The wall 102 defines a distal opening 104. The wall 102 also defines a side opening 106 extending from the outer surface 105 to the inner surface 110. and the inner surface 110 of the wall 102 defines a lumen 108 that extends longitudinally through the catheter 100.

The catheter 100 is flexible to facilitate movement of the catheter 100 through at least a portion of a patient's vasculature. In some embodiments, the catheter 100 includes a reinforcing material to increase stability and rigidity. In certain embodiments, the catheter 100 includes a pre-curved portion that assumes an arcuate profile in the absence of any external forces, facilitating conformity of the catheter 100 to the configuration of a target tissue, such as the blood vessel V shown in FIG. 1, in which the catheter 100 is to be positioned. Alternatively, the catheter 100 may be straight in the absence of any external forces. The catheter may be formed, for example, through injection molding and/or extrusion processes.

The lumen 108 extends through the catheter 100 and has a circular cross-section along the length of the catheter. It should be appreciated, however, that the lumen 108 and the catheter 100 may each assume other configurations without departing from the scope of the present disclosure, as will be discussed in further detail below.

Suitable, non-exclusive examples of catheters 100 include the PALINDROME™ and MAHURKAR®. Maxid™ catheters, each of which is made available by Covidien, which maintains a principal place of business at 15 Hampshire Street, Mansfield, Mass.

With reference now to FIGS. 4-8, the stylet 200 is insertable into the lumen 108 extending through the catheter 100, and includes respective proximal and distal end portions 202, 204, as well as an elongate body 206 defining a passage 210 that extends from the proximal end portion 202 to the distal end portion 204.

The proximal end portion 202 of the stylet 200 is connectable to the fluid source 300 (FIG. 1). Fluid introduced into the proximal end portion 202, from the fluid source 300, moves through the passage 210 extending through the elongate body 206 of the stylet 200. For example, the proximal end portion 202 of the stylet 200 may include a luer adapter 212 connectable to the fluid source 300. The fluid source 300 may be, for example, a syringe and/or a pump. The fluid source 300 may deliver any fluid suitable for facilitating deagglomeration and/or dislodging of the blockage B (FIG. 2). Examples of fluid deliverable by the fluid source 300 to the stylet 200 include saline and an anti-thrombotic fluid, such as heparinized saline.

The distal end portion 204 of the stylet 200 has a closed end 214 and defines one or more apertures 216. The distal end portion 204 also includes a first blocking dam 218 and a second blocking dam 220. The first blocking dam 218 is proximal to the one or more apertures 216, and the second blocking dam 220 is distal to the one or more apertures 216.

Each blocking dam 218, 220 is sealingly engagable with the inner surface 110 of the wall 102 such that the fluid flow is inhibited distally and/or proximally beyond the first and second blocking structures 218, 220. As used herein, the term "blocking dam" refers to a structure spanning the space between the elongate body 206 and the inner surface 110 of the wall. For example, a blocking dam can have an inner surface matching the shape of the elongate body 206 and extends radially from the elongate body 206 to an outer dimension OD matching the shape of the inner surface 110 of the wall 102. Specific examples of blocking dams include toroids, ovals, and D-shaped structures.

The closed end 214 of the stylet 200 prevents the communication of fluid through the distal end portion 204 of the stylet 200, other than through the apertures 216. The closed end 214 of the stylet 200 may include a tapered portion to facilitate, for example, passage of the stylet 200 through the lumen 108 of the catheter 100, and/or passage of the stylet 200 distally beyond the distal opening 104 of the catheter 100 to remove blockage from the distal opening 104.

The one or more apertures 216 are defined by the elongate body 206 of the stylet 200, and may be positioned adjacent the side opening 106 defined by the wall 102 of the catheter 100 via axial movement and/or rotation of the stylet 200 within the catheter 100. The one or more apertures 216 are in communication with the passage 210 such that fluid communicated from the source of fluid 300 (FIG. 1) moves through the passage 210 and exits the stylet 200 through the at least one aperture 216.

The first and second blocking dams 218, 220 are secured to an outer surface 222 of the elongate body 206. For example, the first and second blocking dams 218, 220 can be secured to the outer surface 222 of the elongate body 206 through one or more of monolithic formation, welding, and an adhesive. The first and second blocking dams 218, 220 can be formed from, for example, polyurethane, polypropylene, nylon, synthetic rubber, natural rubber, or any other suitable polymer or elastomeric material. The elongate body 206 may be formed from polypropylene, polyethylene, or polyvinyl chloride (PVC).

Each first and second blocking dam 218, 220 defines an outer transverse dimension OD that is greater than, or equal to, an inner transverse dimension ID defined by the lumen 108 of the catheter 100 such that the first and second blocking dams 218, 220 sealingly engage an inner surface 110 of the lumen 108 upon insertion of the stylet 200 into the catheter 100. In some embodiments, the first and second blocking dams 218, 220 are dimensioned such that the outer transverse dimension OD of each of the first and second blocking dams 218, 220 exceeds the inner transverse dimension ID of the lumen 108 to an extent sufficient to cause deformation of the wall 102 of the catheter 100 in an outward direction, away from a longitudinal axis A defined by the catheter 100. In such embodiments, as the stylet 200 is advanced through the catheter 100, the outward deformation of the wall 102 of the catheter caused by the first and second blocking dams 218, 220 can mechanically disrupt the blockage B (FIG. 2), and/or a fibrin sheath associated with the catheter 100.

The first and second blocking dams 218, 220 may each include an arcuate outer wall 224. As compared to an outer wall with a square profile, such an arcuate outer wall 224 can, for example, reduce friction associated with moving the first and second blocking dams 218, 220 with respect to the inner surface 110 of the lumen 108, thus reducing the force necessary to advance the stylet 200 through the lumen 108 of the catheter 100. Additionally or alternatively, the blocking structures 218, 220 may include a lubricous coating to reduce friction between the first and second blocking dams 218, 220 and the inner surface 110 of the lumen 108.

The first and second blocking dams 218, 220 are spaced axially from one another by a distance L and can be positioned on opposite sides of the one or more apertures 216. For example, the first blocking dam 218 can be proximal to the one or more apertures 216, and the second blocking dam 220 can be distal of the one or more apertures 216. The distance L between the first and second blocking dams 218, 220 will depend on the size of the side opening 106, for example, for the Palindrome™ catheter. In some embodiments, the distance L between the first and second blocking dams 218, 220 is within the range of 0.5-0.25 inches. However, the longer the distance L, the more leeway a clinician will have to place the stylet 200 such that the side opening 106 is between the first and second blocking dams 218, 220.

During use of the stylet 200, fluid communicated from the source of fluid 300 (FIG. 1) enters the passage 210 of the stylet 200 and exits the one or more apertures 216. The seal formed between the first and second blocking dams 218, 220 and the inner surface 110 of the catheter 100 retains the fluid exiting the one or more apertures 216 within a space 226 defined between the inner surface 110 of the lumen 108, the outer surface 222 of the stylet, and the first and second blocking dams 218, 220. The presence of fluid within the space 226 creates a zone of pressure isolated from those portions of the lumen 108 outside of the space 226. The fluid pressure within the space 226 exerts a force upon the blockage B in a radial direction away from the outer surface 222 of the stylet 200 and toward the inner wall 110 of the lumen 108. This radially directed force can deagglomerate (e.g., if the stylet 200 is left in the catheter 100 for a period of time) and/or dislodge the blockage B (FIG. 2) from the side opening 106 defined by the wall 102 of the catheter 100. It should be appreciated, however, fluid may leak past the blocking dams 218, 220 because, for example, the fluid pressure may also cause localized outward deformation of the catheter 100 in the space 226. Fluid introduced into the space 226 through the stylet 200 will still function to remove blockage B even if some of the fluid leaks past the blocking dams 218, 220 and, thus, some leakage is within the scope of the present disclosure.

The elongate body 206 of the stylet 200 has a substantially circular cross-section shape similar to and offset from the shape of the inner surface 110 of the lumen 108 such that the radial spacing between the elongate body 206 and the inner surface 110 is substantially uniform around the circumference of the pressure zone formed between the elongate body 206 and the inner surface 110 of the lumen. This substantially uniform spacing can facilitate introduction of the stylet 200 into the lumen 108 by, for example, reducing the need to orient the stylet 200 with respect to the lumen 108 prior to introduction of the stylet.

Referring now to FIGS. 1-8, an exemplary method of using the stylet 200 includes inserting the stylet 200 into the lumen 108 of the catheter 100, which may be positioned within the blood vessel V. As the stylet 200 is advanced through the lumen 108 of the catheter 100, the first and second blocking dams 218, 220, and in particular, the second blocking dam 220, may act to push any fluid (e.g., lock solution and/or blood) out of the lumen 108 of the catheter 100, potentially contributing to deagglomeration and/or dislodging of the blockage B (FIG. 2).

Figure 6:
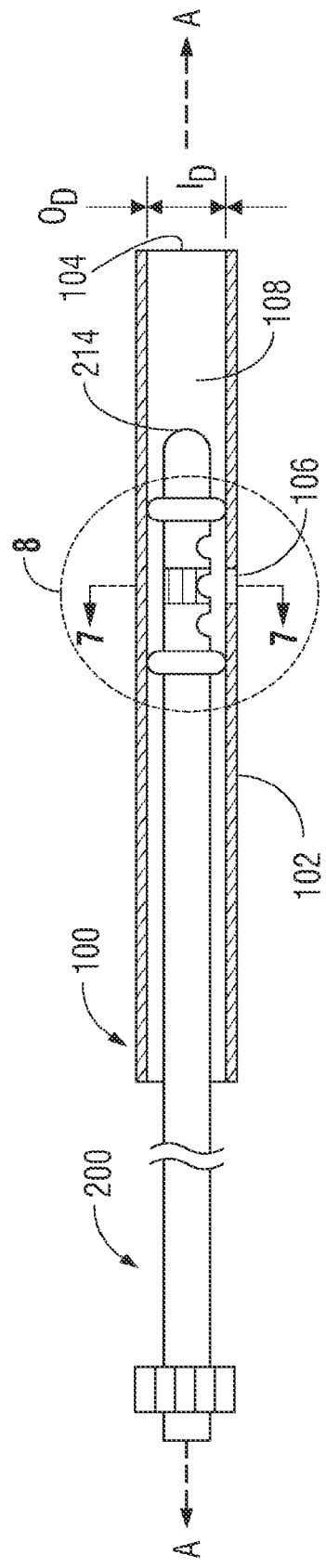
FIG. 6 is a longitudinal, cross-sectional view showing the stylet of FIG. 1 positioned within the catheter of FIG. 1.
Figure 7:
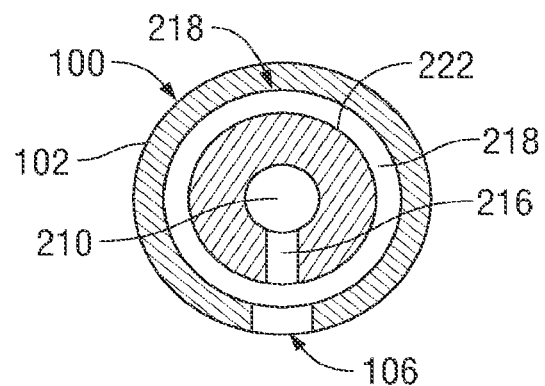
FIG. 7 is a transverse, cross-sectional view taken through lines 7-7 in FIG. 6.
Figure 8:
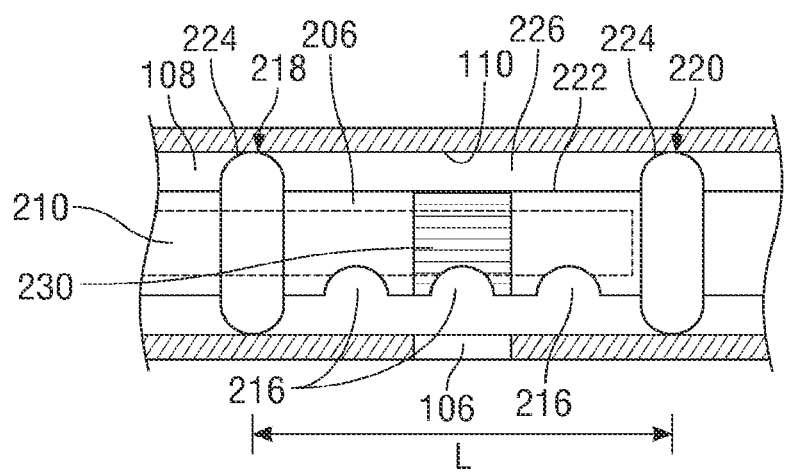
FIG. 8 is an enlargement of the area of detail indicated in FIG. 6.

The stylet 200 is advanced through the lumen 108 of the catheter 100 toward the side opening 106 including the blockage B (FIG. 2), such that the second blocking dam 220 is distal to the opening 106 and the first blocking dam 218 is proximal to the opening 106, as shown in FIGS. 6 and 8, for example. Because the distance L between the blocking dams 218, 220 is greater than the longitudinal dimension of the side opening 106, the stylet 200 does not have to be precisely place and, instead, provides some leeway as to final placement of the stylet 200.

The stylet 200 may be advanced through the lumen 108 until the closed end 214 of the stylet 200 extends distally beyond the catheter 100 to mechanically clear any additional blockage such as, for example, thrombus formed at or near the distal opening 104 of the catheter 100.

To facilitate proper positioning of the stylet 200, the stylet 200 may include a marker band 230 viewable using one or more imaging techniques including fluoroscopy, magnetic resonance imaging (M.R.I.), and/or x-ray. The marker band 230 is located between the first and second blocking dams 218, 220 and extends around at least a portion of the circumference of the elongate body 206. Although the marker band 230 is shown as being adjacent one of the apertures 216 in FIGS. 6 and 8, it should be appreciated that the location of the marker band 230 may be varied without departing from the scope of the present disclosure. For example, the stylet 200 can include one or more marker bands 230 located on either or both of the first and second blocking dams 218, 220. Additionally, or alternatively, one or more portions of the stylet 200 such as, for example, a portion of the stylet 200 between the first and second blocking dams 218, 220, and/or the first and second blocking dams 218, 220 themselves, may be formed from a material more radiopaque than that comprising the remaining portions of the stylet 200.

With the stylet 200 positioned such that the first and second blocking dams 218, 220 are on opposite sides of the side opening 106, fluid is communicated from the source of fluid 300 into the passage 210 of the stylet 200, and through the at least one aperture 216 into the space 226 to create the zone of pressure. As the volume of fluid within the space 226 is increased, increased pressure is applied to the blockage B until the blockage B is successfully dislodged from the side opening 106. In instances wherein the side opening 106 is only partially occluded by the blockage B, increasing the volume of fluid communicated into the space 226 increases the volume of fluid flowing past the blockage B through the side opening 206, further facilitating deagglomeration and/or dislodging of the blockage B.

Using the blocking dams 218, 220 to create the zone of pressure reduces the need for precise longitudinal and/or circumferential alignment of the at least one aperture 216 with the side opening 106.

The stylet 200 can be withdrawn from the lumen 108 (FIGS. 6, 8) of the catheter 100 following, for example, satisfactory dislodging of the blockage B. During withdrawal of the stylet 200, blood may be drawn into the lumen 108 due, for example, to the sealing engagement of the second blocking ring 220 with the inner surface 110 of the lumen 108. This can reduce the likelihood of air infiltration into the catheter 100.

With the stylet 200 withdrawn from the catheter 100, the catheter 100 may be attached to a dialysis machine (not shown) for a dialysis treatment, and/or may be flushed with a solution and clamped, for example, during an interdialytic period.

During manufacture, the stylet 200 may be dimensioned for use with standard length catheters such that the clinician need only advance the stylet 200 as far as it will go into the catheter 100 to place the stylet 200. In such a case, the blocking dams 218, 220 may be closer together as compared to instances in which the stylet 200 is not placed by advancing the stylet 200 as far as it will go into the catheter 100. In the context of reverse tunnel catheters, however, the length of the catheter is often determined after a reverse tunneling procedure, and placement of the catheter. As such, the stylet 200 may be provided with a length longer than the catheter and the at least one aperture 216 may be advanced until it is approximately adjacent the side opening 106, which can be done under fluoroscopy. Specifically, while the back end of the catheter is cut in a reverse tunneling procedure, the distance between a distal opening and a side opening 106 is constant in any specific catheter. Thus, the clinician need only watch for the distal end 214 of the stylet 200 to extend from the catheter 100, or use marker bands if included on the stylet 200.

While certain embodiments have been described, other embodiments are possible.

Figure 9:
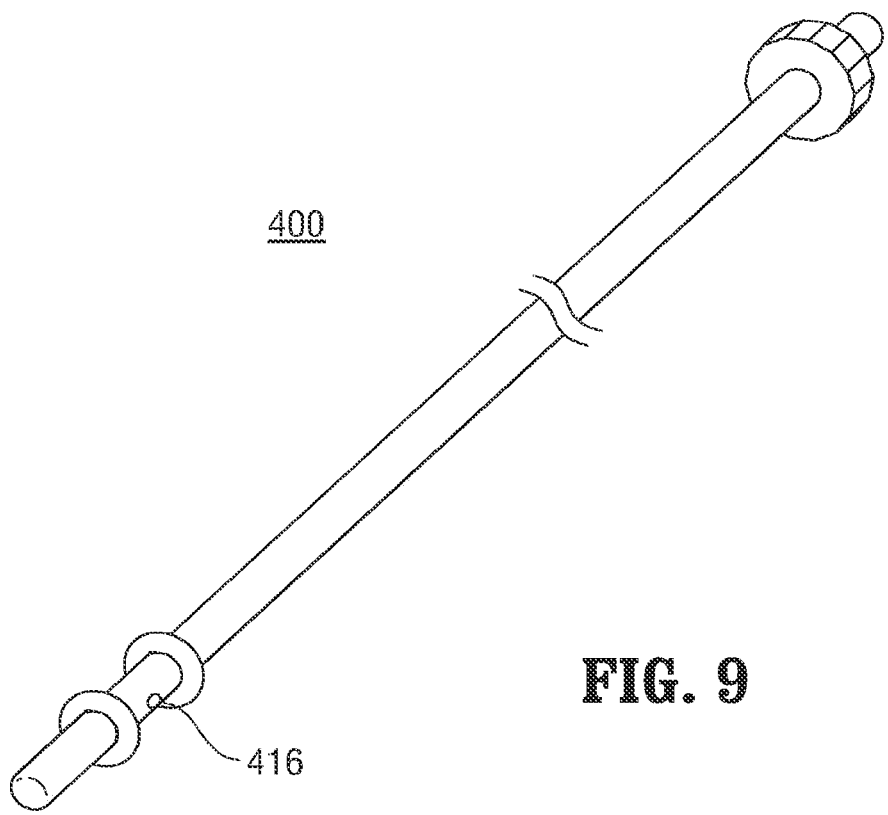
FIG. 9 is a side, perspective view of a stylet.
Figure 10:
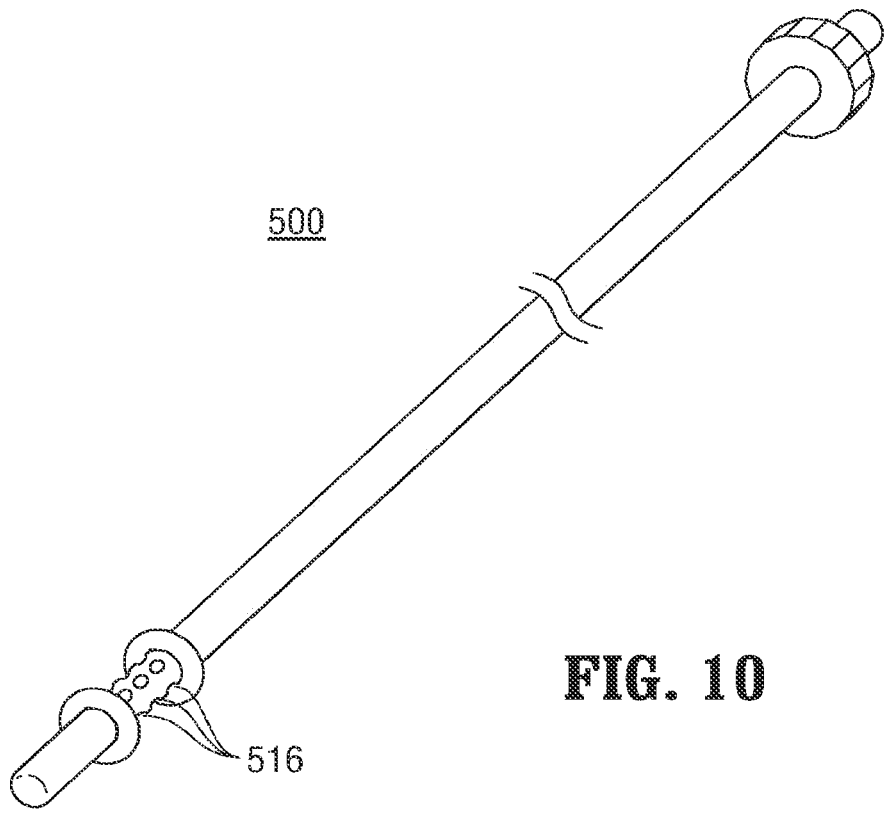
FIG. 10 is a side, perspective view of a stylet.
Figure 11:
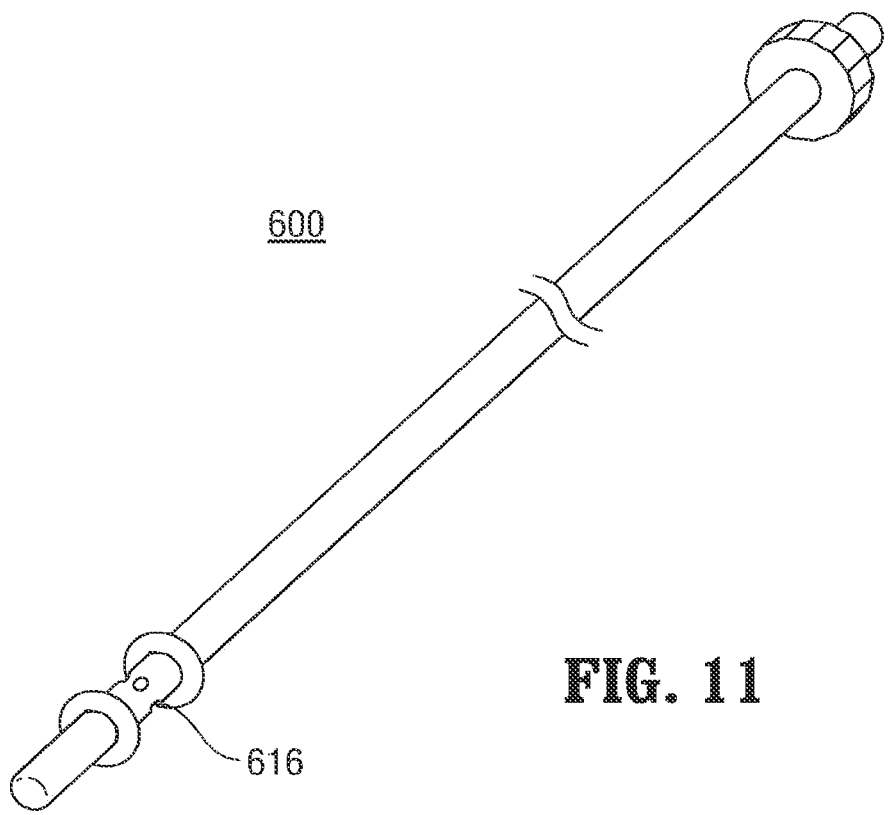
FIG. 11 is a side, perspective view of a stylet.
Figure 12:
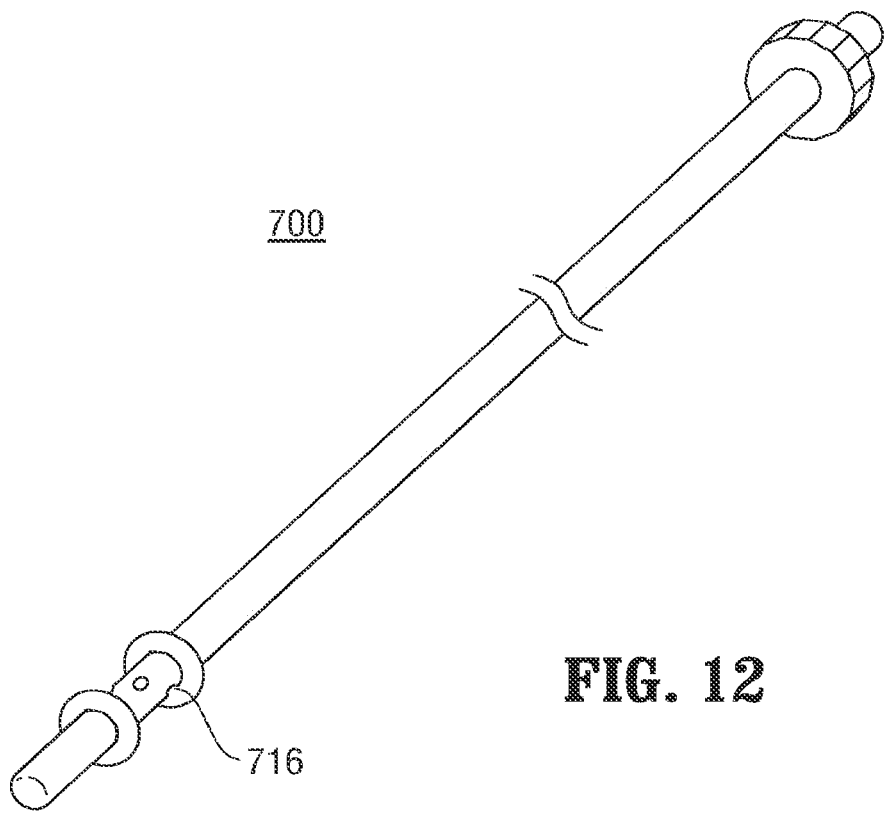
FIG. 12 is a side, perspective view of a stylet.

For example, in FIGS. 6 and 8, the stylet 200 is shown as including three apertures 216 in longitudinal alignment with one another, and arranged in a single row. However, because a zone of pressure is used to clear the blockage B from the catheter 100, the apertures 216 may be present in greater or fewer numbers, and/or may be configured in other orientations. For example, as shown in FIG. 9, a stylet 400 defines a single aperture 416 only and, as shown in FIG. 10, a stylet 500 defines multiple rows of apertures 516 in longitudinal alignment with each other. Referring to FIG. 11, a stylet 600 defines a plurality of apertures 616 in circumferential alignment with each other. As shown in FIG. 12, a stylet 700 defines a plurality of apertures 716 circumferentially and axially offset from one another, for example, in a helical pattern. As another example, while stylets have been described as being used in single lumen catheters, other embodiments are additionally or alternatively possible. For example, with reference to FIGS. 13, 13A, and 14A a stylet 900 can be used with a catheter 1000 that defines a first lumen 1002 and a second lumen 1006. The first lumen 1002 can be, for example, an arterial lumen, and the second lumen 1006 can be, for example, a venous lumen. The first lumen 1002 is in fluid communication with a side opening 1004, and the second lumen 1006 is in fluid communication with another side opening (not shown in FIG. 13). The lumens 1002, 1006 of the catheter 1000 are each D-shaped, and are separated by a septum wall 1010. To facilitate use with the catheter 1000, the stylet 900 includes a body 906 that defines a D-shaped cross-section. The stylet 900 may include a first blocking dam 904 and a second blocking dam 908, which are also both D-shaped, as shown in FIGS. 14A-14C, to conform to the lumens 1002, 1006 and retain fluid between the blocking dams 904, 908.

With reference to FIGS. 13 and 14A-14C, the body 906 of the stylet 900 may be either partially or fully encircled by the blocking dams 904, 908. For example, in FIG. 14A, the body 906 of the stylet 900 is shown as being partially encircled by the blocking dam 908. Alternatively, with reference to FIG. 14B, a stylet 900' is shown that includes a body 906' that is fully encircled by a blocking dam 908'. The body 906' of the stylet 900' and the blocking dams, e.g., the blocking dam 908', may include corresponding configurations, as shown in FIG. 14B. Alternatively, with reference to FIG. 14C, a stylet 900" is shown that includes a body 906" having a first configuration, e.g., a circular cross-section, and a blocking dam 908" having a second, different configuration, e.g., a D-shaped cross-section.

Figure 15:
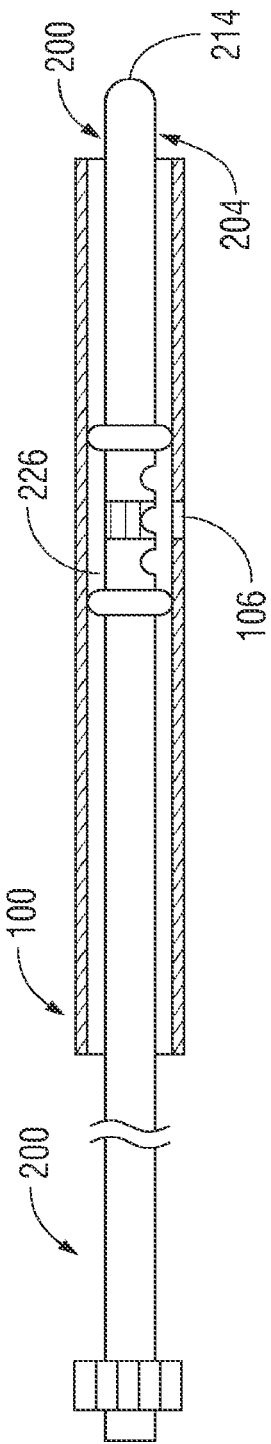
FIG. 15 is a longitudinal, cross-sectional view of a stylet positioned within the catheter.

While only a single stylet 900 is shown in FIG. 13, two such stylets may be employed. For example, one stylet 900 may be used for each of the lumens 1002, 1006 and may be inserted into, and manipulated within, the lumens 1002, 1006 either independently, or simultaneously. As yet another example, stylets may be dimensioned such that the stylet can be extended distally beyond a catheter to facilitate, for example, removal of a blockage from a distal opening of the catheter while clearing a blockage from a side opening of the catheter. Referring to FIG. 15, for example, the distal end portion 204 of the stylet 200 may be dimensioned such that the closed end 214 extends distally beyond the catheter 100 upon positioning of the side opening(s) 106 within the space 226.

Persons skilled in the art will understand that the devices and methods specifically described herein, and shown in the accompanying drawings, constitute non-limiting, exemplary embodiments of the present disclosure, and that the elements and features shown or described in connection with one exemplary embodiment may be combined with those of another embodiment without departing from the scope of the present disclosure.

As well, one skilled in the art will appreciate further features and advantages of the presently disclosed stylet based on the above-described embodiments and the claims. Accordingly, the present disclosure is not limited by what has been particularly shown and described.

What is claimed is:

1. A stylet comprising:
an elongate body defining a passage and a plurality of apertures in fluid communication with the passage;
a first blocking dam secured to the elongate body entirely proximal to the plurality of apertures; and
a second blocking dam secured to the elongate body entirely distal to the plurality of apertures, wherein the first and second blocking dams each defines a D-shaped cross-section,
wherein the first and second blocking dams are circumferentially aligned, and
wherein the elongate body is configured to be movable within a lumen of a catheter to a position in which the first and second blocking dams are, respectively, proximal and distal to a side opening of the catheter and each of the first and second blocking dams is sealingly engageable with an inner surface of the catheter such that fluid introduced into the lumen of the catheter, from the passage and through the plurality of apertures of the stylet, is directed through the side opening of the catheter.

2. The stylet of claim 1, wherein the plurality of apertures includes apertures axially aligned with one another along a longitudinal axis of the elongate body.

3. The stylet of claim 1, wherein the plurality of apertures includes apertures disposed about a circumference of the elongate body.

4. The stylet of claim 1, wherein the plurality of apertures includes apertures circumferentially and axially offset from each other.

5. The stylet of claim 1, wherein each of the first and second blocking dams includes an arcuate outer wall configured to engage with the inner surface of the catheter.

6. The stylet of claim 1, wherein each of the first and second blocking dams has a lubricous coating.

7. The stylet of claim 1, wherein the elongate body includes a closed distal end.

8. The stylet of claim 1, further comprising a marker band extending around at least a portion of a circumference of the elongate body.

9. The stylet of claim 1, wherein the first and second blocking dams are formed from a material more radiopaque than the elongate body.

10. The stylet of claim 1, wherein the elongate body defines a D-shaped cross-section.

11. The stylet of claim 1, wherein the elongate body defines a circular cross-section.

12. The stylet of claim 1, wherein at least one of the first blocking dam or the second blocking dam only partially encircles an outer perimeter of the elongate body.

13. The stylet of claim 1, wherein the first blocking dam or the second blocking dam fully encircles an outer perimeter of the elongate body.

14. The stylet of claim 1, wherein each of the first and second blocking dams is formed from polyurethane, polypropylene, nylon, synthetic rubber, or natural rubber.

15. The stylet of claim 1, wherein at least one of the first blocking dam or the second blocking dam is monolithically formed with the elongate body.

16. The stylet of claim 1, wherein at least one of the first blocking dam or the second blocking dam is welded or adhered to the elongate body.

17. A system comprising:
the stylet of claim 1;
a fluid source; and
the catheter, wherein the elongate body of the stylet is configured to fluidically connect to the fluid source and deliver the fluid from the fluid source to the lumen of the catheter via the passage and the plurality of apertures.

18. A system comprising
the catheter defining the lumen, wherein the lumen is D-shaped; and
the stylet of claim 1, wherein the first and second blocking dams conform to the D-shaped lumen and are configured to retain fluid between the first and second blocking dams when the elongate body and the first and second blocking dams are inserted in the lumen of the catheter.

19. A stylet comprising:
an elongate body defining a passage and a plurality of apertures in fluid communication with the passage;
a first blocking dam secured to the elongate body entirely proximal to the plurality of apertures; and
a second blocking dam secured to the elongate body entirely distal to the plurality of apertures, wherein each of the first and second blocking dams only partially encircles an outer perimeter of the elongate body,
wherein the first and second blocking dams are circumferentially aligned, and
wherein the elongate body is configured to be movable within a lumen of a catheter to a position in which the first and second blocking dams are, respectively, proximal and distal to a side opening of the catheter and each of the first and second blocking dams is sealingly engageable with an inner surface of the catheter such that fluid introduced into the lumen of the catheter, from the passage and through the plurality of apertures of the stylet, is directed through the side opening of the catheter.

20. A system comprising:
a catheter defining a lumen and a side opening, wherein the lumen is D-shaped; and
a stylet comprising:
an elongate body defining a passage and a plurality of apertures in fluid communication with the passage;
a first blocking dam secured to the elongate body proximal to the plurality of apertures; and
a second blocking dam secured to the elongate body distal to the plurality of apertures, wherein the first and second blocking dams each defines a D-shaped cross-section,
wherein the elongate body is configured to be movable within the lumen of the catheter to a position in which the first and second blocking dams are, respectively, proximal and distal to the side opening of the catheter and each of the first and second blocking dams is sealingly engageable with an inner surface of the catheter such that fluid introduced into the lumen of the catheter, from the passage and through the plurality of apertures of the stylet, is directed through the side opening of the catheter, and
wherein the first and second blocking dams conform to the D-shaped lumen and are configured to retain fluid between the first and second blocking dams when the elongate body and the first and second blocking dams are inserted in the lumen of the catheter.

* * * * *